United States Patent [19]

Albright et al.

[11] Patent Number: 4,696,963
[45] Date of Patent: Sep. 29, 1987

[54] HALOGENATED ALKYL PHOSPHATE ESTERS AND POLYMER SYSTEMS INCORPORATING THEM

[75] Inventors: James A. Albright, San Leandro, Calif.; Theodore C. Wilkinson, Dublin, Ohio

[73] Assignee: Great Lakes Chemical Corporation, West Lafayette, Ind.

[21] Appl. No.: 786,208

[22] Filed: Oct. 10, 1985

[51] Int. Cl.$^4$ .............................................. C08K 5/53
[52] U.S. Cl. .................... 524/144; 252/609; 521/107
[58] Field of Search .............. 252/609; 521/107; 524/149

[56] References Cited

U.S. PATENT DOCUMENTS

| | | | |
|---|---|---|---|
| 3,132,169 | 5/1964 | Birum et al. | 558/91 |
| 3,192,242 | 6/1965 | Birum | 558/91 |
| 3,324,205 | 6/1967 | Carpenter et al. | 558/91 |
| 3,344,112 | 9/1967 | Birum | 524/145 |
| 3,453,348 | 7/1969 | Demarcq et al. | 558/97 |
| 3,781,388 | 12/1973 | Jenkner et al. | 558/177 |
| 3,830,886 | 8/1974 | Davis et al. | 558/177 |
| 3,978,167 | 8/1976 | Albright | 558/77 |
| 3,997,449 | 12/1976 | Wilkinson | 252/609 |
| 4,046,719 | 9/1977 | Stanaback et al. | 521/155 |
| 4,083,825 | 4/1978 | Albright et al. | 524/144 |
| 4,083,826 | 4/1978 | Albright | 523/506 |
| 4,144,387 | 3/1979 | Anderson et al. | 252/609 |
| 4,240,953 | 12/1980 | Albright | 524/144 |
| 4,242,288 | 12/1980 | Weil | 521/107 |
| 4,458,034 | 7/1984 | Fracalossi et al. | 521/107 |
| 4,510,101 | 4/1985 | Pawlosky et al. | 528/51 |
| 4,565,833 | 1/1986 | Buszard et al. | 521/107 |

FOREIGN PATENT DOCUMENTS 2416663 8/1974 Fed. Rep. of Germany .

Primary Examiner—John Kight
Assistant Examiner—Kriellion Morgan
Attorney, Agent, or Firm—Kirkland & Ellis

[57] ABSTRACT

Flame retardant non-mutagenic halogenated alkyl phosphate ester mixture of the formula:

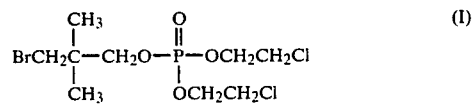

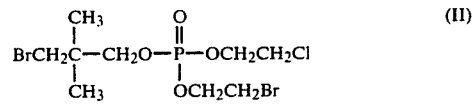

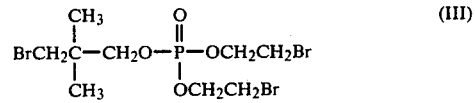

and flame retardant polymer systems incorporating such mixtures.

8 Claims, No Drawings

HALOGENATED ALKYL PHOSPHATE ESTERS AND POLYMER SYSTEMS INCORPORATING THEM

BACKGROUND OF THE INVENTION

1. Field of the Invention

The present invention relates to mixtures of halogenated alkyl phosphate esters containing aliphatic bromine and chlorine which may be used to flame-retard polymeric systems such as flexible polyurethanes, reaction injection molded polyurethanes, polyvinyl chloride, textile fibers, and poly-(methylmethacrylate), and the like.

2. Description of the Prior Art

The need to reduce the flammability of polymeric systems while not adversely affecting the chemical, physical and mechanical properties or the appearance of polymeric systems is disclosed in the *Encyclopedia of Polymer Science and Technology*, Volume 7, pp. 1–3 and the *The Encyclopedia of Chemical Technology*, 3rd Edition, Volume 10, pg. 348.

Phosphorous-halogen systems have been widely used to flame retard polymeric systems. For example, the use of certain pentavalent phosphate esters containing bromine and chlorine as flame retardants is taught by Birum, et al., U.S. Pat. No. 3,132,169. The compounds of Birum are selected from the general formula:

$$\text{Br}-\overset{\overset{R}{|}}{\underset{\underset{R}{|}}{C}}-\left[\overset{\overset{R'}{|}}{\underset{\underset{R'}{|}}{C}}\right]_n-\overset{\overset{R}{|}}{\underset{\underset{R}{|}}{C}}-O-\overset{O}{\underset{}{\overset{\|}{P}}}\underset{\underset{R''\ R''}{|\ \ |}}{\overset{\overset{R''\ R''}{|\ \ |}}{\underset{}{{}^{OCHCHBr}_{OCHCHCl}}}}$$

wherein R is selected from the class consisting of hydrogen, alkyl and haloalkyl radicals of from 1 to 2 carbon atoms, R' is selected from the class consisting of hydrogen, alkyl and haloalkyl radicals of from 1 to 5 carbon atoms, R" is selected from the class consisting of R' and hydrocarbyloxymethyl radicals of from 1 to 8 carbon atoms, wherein one R" at a pair of adjacent carbon atoms must be hydrogen, and n is an integer from 0 to 1.

Other patents disclosing halogenated phosphate esters include Birum U.S. Pat. Nos. 3,192,242 and 3,344,112; Carpenter U.S. Pat. No. 3,324,205; Jenkner et al. U.S. Pat. No. 3,781,388; Dow et al. U.S. Pat. No. 3,830,886; Wilkinson U.S. Pat. No. 3,997,449; Stanaback U.S. Pat. No. 4,046,719; Albright U.S. Pat. Nos. 4,083,826 and 4,240,953; and West German OS Pat. No. 2,416,663. Applicants' own U.S. Pat. No. 4,083,825 discloses the use of bis(2-chloroethyl) 2,2-dimethyl-3-bromopropyl phosphate as a flame retardant for polyurethane foams.

None of the foregoing halogenated alkyl phosphate esters are believed to perform as effectively as desired as flame retardant additives. Furthermore, numerous halogenated alkyl phosphates containing aliphatic bromine have been determined to be mutagenic by the Ames test. On Apr. 28, 1977, the Consumer Products Safety Commission, acting under the Federal Hazardous Substances Act, banned the sales of children's sleepwear treated with the flame-retardant tris-(2,3-dibromopropyl) phosphate ("Tris"). In explaining this action, the Commission cited the two-year feeding tests by the National Cancer Institute that linked Tris to kidney cancer in mice and rats. It also cited studies showing that Tris, when tested in the Ames Test, was mutagenic in bacteria and, thus, possibly carcinogenic in humans.

It is, thus, a primary object of this invention to provide highly effective flame retardant mixtures of halogenated alkyl phosphates.

It is another object of the present invention to provide a mixture of halogenated alkyl phosphate esters containing aliphatic bromine which are not mutagenic by the Ames Test.

It is also an object of the present invention to provide effectively flame-retarded polymeric systems which do not possess any undesirable chemical, physical and mechanical properties and whose appearance is substantially unchanged by the flame retardant that is employed.

SUMMARY OF THE INVENTION

The foregoing and other objects, advantages, and features of this invention may be achieved with flame retardant non-mutagenic mixtures consisting essentially of compounds of the formula:

$$\text{BrCH}_2\overset{\overset{CH_3}{|}}{\underset{\underset{CH_3}{|}}{C}}-\text{CH}_2\text{O}-\overset{O}{\underset{\underset{OCH_2CH_2Cl}{|}}{\overset{\|}{P}}}-\text{OCH}_2\text{CH}_2\text{Cl} \quad (I)$$

$$\text{BrCH}_2\overset{\overset{CH_3}{|}}{\underset{\underset{CH_3}{|}}{C}}-\text{CH}_2\text{O}-\overset{O}{\underset{\underset{OCH_2CH_2Br}{|}}{\overset{\|}{P}}}-\text{OCH}_2\text{CH}_2\text{Cl} \quad (II)$$

$$\text{BrCH}_2\overset{\overset{CH_3}{|}}{\underset{\underset{CH_3}{|}}{C}}-\text{CH}_2\text{O}-\overset{O}{\underset{\underset{OCH_2CH_2Br}{|}}{\overset{\|}{P}}}-\text{OCH}_2\text{CH}_2\text{Br} \quad (III)$$

The foregoing mixtures preferably embody the Compounds (I), (II), and (III) in the following ratios, as determined by vapor phase chromatography ("VPC") area analysis:

Compound (I)—1.0.
Compound (II)—1.5
Compound (III)—1.0

This invention further includes novel methods of preparing such mixtures by reacting neopentyl glycol with phosphorous trichloride, the resulting intermediate then being reacted first with bromine to form a halogenated phosphorous monoester and, thereafter, with ethylene oxide to yield the desired mixture of compounds, which is then then isolated from the reaction mixture, purified and stabilized.

The invention also comprises flame retarded polymer systems incorporating effective amounts of the mixtures of this invention, such polymer systems including flexible polyurethanes, reaction injection molded polyurethanes, polyvinyl chloride, textile fibers, poly-(methyl)-(methacrylate), and the like.

DETAILED DESCRIPTION OF THE INVENTION

Flame-retardant halogenated alkyl phosphate esters of this invention which have improved flame retarding efficiency and are not mutagenic by the Ames Test comprise a mixture consisting essentially of compounds of the formula:

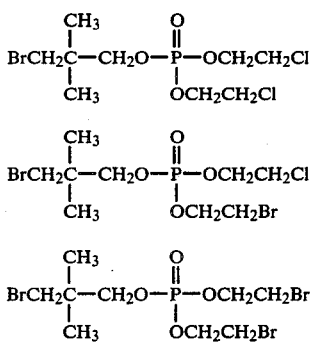

Most desirably, Compounds (I), (II), and (III) are present in the mixture in a VPC area ratio of about 1.0:1.5:1.0.

The invention mixture of these compounds may be prepared by reacting phosphorous trichloride with neopentyl glycol to form a cyclic phosphorous compound of the formula:

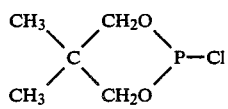

The cyclic phosphorous compound is then reacted with bromine to cleave the cyclic structure and produce a ring-opened halogenated phosphorous monoester of the formula:

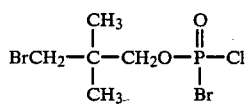

The ring-opened halogenated phosphorous monoester is then reacted with ethylene oxide to form the mixture of compounds of the present invention:

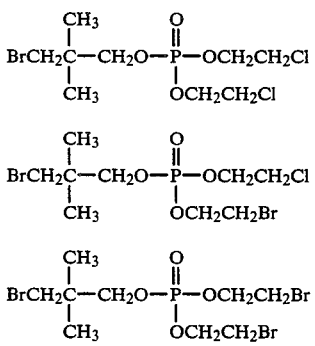

The mixture is then isolated, purified and stabilized.

The foregoing reactions generally proceed quite readily and usually no special reaction conditions or chemical processing equipment need be employed. These reactions can be conducted at room temperature, at temperatures above ambient, or at temperatures below ambient. Elevated temperatures may be used to ensure completion of the reaction, although some of the foregoing condition reactions are quite exothermic, and it may be advisable, at least initially, to provide external cooling. It may be preferable, although not essential, to employ solvents such as halogenated hydrocarbon solvents (e.g., methylene chloride and chlorobenzene).

While the presence of a catalyst is generally not required, catalysts may decrease reaction times and allow the use of lower reaction temperatures. In particular, the final step of reacting the halogenated phosphorous monoester with ethylene oxide is facilitated by using a small but catalytically effective amount of titanium tetrachloride or other catalysts such as tin tetrachloride or magnesium chloride.

After the halogenated phosphorous monoester is completely reacted with ethylene oxide to form the mixture of this invention, the mixture is then isolated, purified and stabilized. Isolation and purification may be carried out by washing with water, aqueous ammonia or the like, adjusting the pH to a consistent value in the range of about 9-10 and separating and recovering the low viscosity liquid product mixture by phase separation and filtration.

Advantageously, the product mixture is acid stabilized by adding a small but effective amount (e.g., about 0.1–5.0 weight percent, preferably about 0.5–2.0%) of an acid stabilizer such as ERL-4221, a cycloaliphatic expoxide commercially available from Union Carbide Corporation. Other acid stabilizers such as epoxidized soybean oil, phenyl glycidyl ether, epibromohydrin, and the diglycidyl ether of tetrabromobisphenol A may also be used.

The following examples are provided for the purpose of further illustration of the preferred embodiments of the present invention and are not intended to be limitations on the disclosed invention.

EXAMPLE 1

To 142.82 g. (1.04 mole) of phosphorous trichloride, a solution of 104.1 g. 1.00 mole) neopentyl glycol and 188 ml. of methylene chloride maintained at 38° C., was added dropwise while the reaction mixture was maintained at or below 10° C. Once the addition was complete, the reaction mixture was heated to 30° C. and maintained at this temperature for one-half hour. The methylene chloride was then removed from the reaction mixture under aspirator vacuum. After cooling the reaction mixture to 20° C., 160 g. of bromine (1.00 mole) was added while the reaction temperature was maintained below 20° C. with the cooling. Titanium tetrachloride catalyst, 1.9 g. (0.01 mole) was then added, and ethylene oxide addition started immediately. The reaction temperature was maintained below 65° C. and ethylene oxide addition continued until the exothermic reaction subsided. A total of 165.8 g. (3.8 mole) ethylene oxide was added. The product was washed with aqueous ammonia and the separated from the aqueous layer. After vacuum drying, one percent by weight of ERL-4221 as an acid stabilizer was added to the product and thoroughly mixed. The product yield was 98% based on neopentyl glycol.

Analysis of the unstabilized product shows: 37.82% bromine (38.4% theor.); 8.13% chlorine (8.5% theor); 0.2% water; acid no. 0.01 milligrams KOH per gram. Analysis of the product by vapor phase chromatopography area analysis showed that three primary components were present.

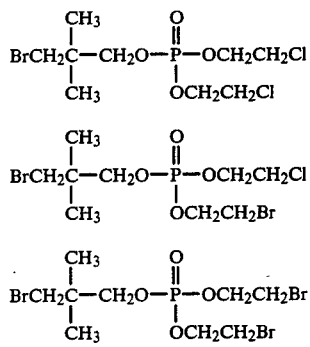

The ratio of the three compounds (I):(II):(III) in this product was found be about 1.0 to about 1.5 to about 1.0 as determined by VPC area analysis.

EXAMPLE 2

To 145.6 g. (1.06 mole) of phosphorous trichloride cooled to 5° C., 104.1 g. (1.00 mole) of neopentyl glycol (solid) was added at an even rate so that the reaction temperature was maintained below 7° C. Once the addition was complete, the reaction mixture was held below 7° C. for 60 minutes. The reaction mixture was then heated to 30° C. for 30 minutes and finally vacuum stripped at 30° C. for 30 minutes. Bromine 159.8 g., (1.00 mole) was then added while the reaction mixture was held below 30° C. Next, the mixture was heated to 50° C. and vacuum stripped for 30 minutes. After cooling to ambient temperature, 1.9 g. (0.01 mole) of titanium tetrachloride was added, and 98.7 g. (2.24 mole) ethylene oxide was added subsurface while the reaction temperature was held below 85° C. with cooling. The reaction mixture was then held at 85° C. for 30 minutes. After cooling, the product was washed with aqueous ammonia and then separated from the aqueous layer. After vacuum drying, one percent by weight of ERL-4221 as an acid stabilizer was added to the product and thoroughly mixed. The product yield was 95% based on neopentyl glycol. Analysis of the unstabilized product shows: 37.2% bromine (38.4% theor.); 8.3% chlorine (8.5% theor.); 0.1% water; acid no. 0.04 milligrams KOH per gram. Distribution of compounds in the product mixture was: 1.0:1.5:0.9 (I:II:III), as determined by VPC area analysis.

EXAMPLE 3

Mutagenicity Testing

Three different samples of phosphate mixtures prepared in accordance with Example 1 were tested for mutagenic activity in a series of in vitro microbial assays employing Salmonella indicator organisms. Also, one such sample was tested for mutagenicity in the in vitro transformation of BALB 3T3 by the technique well known to those skilled in the art. When tested in this manner, the phosphate mixture of the present invention did not exhibit genetic activity in any of the assays conducted, nor was it mutagenic under these test conditions. (See Ames, B. N. McCann, J. and Yamasaki, E., "Methods for Detecting Carcinogens and Mutagens with the Salmonella/Mammalian-Microsome Mutagenicity Test" Mutation Research, 31, 347-64 (1975)). This result was most surprising because a number of related halogenated phosphates have been studied and found to be mutagenic by the Ames Test. Compounds in this class include bis(2,3-dibromopropyl) 2,2-bis(-bromomethyl)-3-chloropropyl phosphate, which is specifically disclosed in Example 2 in U.S. Pat. No. 4,240,953. Moreover, 3-bromo-2,2-dimethylpropyl 1-bromo-2-propyl 1-chloro-2-propyl phosphate, disclosed in Example 2 of Birum U.S. Pat. No. 3,132,169, has also been found to be mutagenic to strain TA1535 in activation assays. And 3-bromo-2, 2-dimethylpropyl 1-bromo-3-chloro-2-propyl 1,3-dichloro-2-propyl phosphate disclosed in Applicant's U.S. Pat. No. 4,083,825 has been evaluated and, likewise, shown to be mutagenic.

APPLICATIONS

The halogenated alkyl phosphate mixtures of the present invention may be used as flame retardants in a wide variety of natural and synthetic polymeric systems including amino resins, cellulose acetate, epoxy resins, acrylic latexes, SBR Rubber, vinyl acetate latexes, nitrocellulose lacquer, paper, phenolic resins, unsaturated polyester, poly-(methylmethacrylate), nitrile rubber, urethane coatings, flexible polyvinyl chloride, flexible polyurethane foam, bonded polyurethane foam, rigid polyurethane foam, reaction injection molded ("RIM") polyurethanes, polystyrene foam, fabric containing formulations, and wood.

The flame retardant mixture of this invention may be incorporated into or applied onto virtually any flammable polymeric material by techniques which are standard or known to those skilled in the art. See, for example. J. M. Lyons, "The Chemistry and Uses of Fire Retardants", Wiley-Interscience, New York, NY (1970), and Z. E. Jolles, "Bromine and Its Compounds", Academic Press, New York, NY (1966).

Depending on the substrate and the amount of flame retardancy desired, up to about 40 weight percent of the flame retardant mixture may be incorporated therewith. However, in most applications, it is preferred to use less than 25 weight percent of compounds within the scope of this invention. It should be noted that the optimum level of additive of the flame retardant mixture within the scope of this invention depends upon the particular substrate being treated as well as the level of flame retardancy desired. For example, in polyurethanes, a flame retardant level of from about 0.5–12 percent by weight of the total polymeric composition is satisfactory.

It is to be understood that the term polyurethanes as used herein means polymers containing repeated urethane linkages:

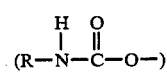

where R is an aromatic or aliphatic group. These polymers are generally made by reacting a polyisocyanate with a compound having a plurality of hydroxyl groups.

Thus the polyurethanes used in the present invention compositions are any polyurethane herein defined and which one so desires to flame retard,. It is to be understood that the polyurethanes used can be a "virgin" material, i.e., substantially free of additives such as stabilizers, platicizers, dyes, pigments, fillers, and the like, or the polyurethanes can have additives (such as those mentioned and described herein) already contained therein or added concurrently with or after the addition of the phosphate compounds of formula I. These polyurethane compositions include: rigid foams, semi-rigid foams, flexible foams, rubbers and adhesives.

The phosphate mixtures of this invention are particularly effective in flexible polyurethane foams and RIM polyurethane.

It is also within the scope of the present invention to employ other materials in the present invention compositions where one so desires to achieve a particular end result. Such materials include, without limitation, adhesion promotors; antioxidants; antistatic agents; antimicrobials; colorants; plasticizers, etc., such as those listed on pages 594-655; Modern Plastics Encyclopedia, 1984-1985; (in addition to the new class of flame retardants described herein); heat stabilizers; light stabilizers; pigments; plasticizers; preservaties; ultraviolet stabilizers and fillers. In this latter category, i.e., fillers, there can be mentioned without limitation, materials such as glass, carbon, cellulosic fillers (wood flour, cork, and shell flour); calcium carbonate (chalk, limestone, and preciptated calcium carbonate); metal flakes; metallic oxides (aluminum, beryllium oxide and magnesia); metallic powders (aluminum, bronze, lead, stainless steel and zinc); polymers (comminuted polymers and elastomerplastic blends); silica products (diatomaceous earth, novaculite, quartz, sand, tripoli, fumed colloidal silica, silica aerogel, wet process silica); silicates (asbestos, kaolimite, mica, nepheline syenite, talc, wollastonite, aluminum silicate and calcium silicate); and inorganic compounds such as barium ferrite, barium sulfate, molybdenum disulfide and silicon carbide.

The above mentioned materials including filler, are more fully described in Modern Plastics Encyclopedia, ibid., and which publication has been incorporated herein in toto by reference.

The amount of the above described materials employed in the present invention compositions can be any quantity which will not substantially adversely affect the desired results derived from the present invention compositions. Thus, the amount used can be any amount up to that percent based on the total weight of the composition at which said composition can still be classified as a plastic. In general, such amount will be from about 0% to about 75% and more specifically from about 1% to about 50%.

For a detailed description of various polyurethane preparations of specific elastomers and specific rigid and flexible foams, one is directed to the literature and patents wherein may be found numerous such detailed descriptions, e.g., K. C. Frisch and J. H. Saunders, "Plastic Foams", Vol 1, parts 1 and 2, Marcel Dekker, Inc., New York, NY, 1972 and T. H. Ferrigno, "Rigid Plastic Foams", Second Edition, Reinhold Publishing Corp., New York, 1967.

The following examples are provided for the purpose of further illustration of polymer applications employing the mixtures of this invention.

EXAMPLE 4

Polyurethane Foams for Automotive Applications

Polyurethane foams were prepared using a conventional one-shot process employing the invention mixture of Example 1 and, for comparative purposes, tris(1,3 dichloroisopropyl) phosphate using the following formulation:

| Component | Parts By Weight |
|---|---|
| 3,000 MW Glycerin-Based Heteropolyol | 100 |
| Water | 4.5 |
| Trichlorofluoromethane | 9.0 |
| Stannous Octoate | 0.2 |
| Flame Retardant | See Table I |
| Silicone Surfactant | 1.0 |
| Tertiary Amine | See Table I |
| Toulene Diisocyanate | 57.7 |

TABLE I

| Flame Retardant | Amine Catalyst | Density | Air Flow | Flammability* |
|---|---|---|---|---|
| 6 parts Invention Mixture (Example 1) | 0.26 | 1.24 lb/ft$^3$ | 6.9 | Pass |
| 9 parts Tris (1,3-dichloro-isopropyl) phosphate | 0.22 | 1.26 | 6.2 | Fail |

*Flammability of foams tested per Motor Vehicle Safety Standard 302.

As the foregoing data demonstrate, the mixture of this invention was found to be significantly more efficient than another halogenated aliphatic phosphate under similar conditions.

EXAMPLE 5

Polyurethane Foams for Automotive Applications

Polyurethane foam samples were prepared using a conventional one-shot process employing the following formulation using the invention mixture (Example 1) and, for comparative purposes, bis(2-chloroethyl)2,2-dimethyl-3-chloropropyl phosphate:

| Component | Parts by Weight |
|---|---|
| Dow 4291 Polyol | 100 |
| Silicone Surfactant | 1.5 |
| Water | 4.3 |
| Tertiary Amine | See Table II |
| Toluene Diisocyanate | 52.9 |
| Stannous Octoate | 0.06 |

TABLE II

| Flame Retardant | Amine Catalyst | Density | Flammability* |
|---|---|---|---|
| 2.5 Parts Invention Mixture (Example 1) | 0.45 | 2.0 lb/ft$^3$ | Pass |
| 5.0 Parts Bis (2-chloroethyl)2,2-Dimethyl 3-Chloropropyl Phosphate | 0.45 | 2.0 lb/ft$^3$ | Fail |

*Flammability of foams tested per Motor Vehicle Safety Standard 302

As the foregoing data demonstrate, the mixture of this invention is a significantly more effective flame retardant than the prior art fully chlorinated analog.

EXAMPLE 6

Polyurethane Foam For Furniture Application

Foams were again prepared using a conventional one-shot process employing the formulations given below. In addition to the invention mixture (Example 1), foams were prepared for comparative purposes using Compound I, the prior art bis(2-chloroethyl)2,2-dimethyl-3-bromopropyl phosphate of Applicant's U.S. Pat.

No. 4,083,825, and a commercially available pentabromodiphenyl ether/aromatic phosphate blend.

| Component | Parts by Weight |
|---|---|
| 3,000 MW Glycerin-Based Heteropolyol | 100 |
| Water | 4.5 |
| Trichlorofluoromethane | 4.0 |
| Stannous Octoate | 0.16 |
| Flame Retardant | See Table III |
| Silicone Surfactant | 1.0 |
| Tertiary Amine | See Table III |
| Toluene Diisocyanate | 57.7 |

TABLE III

| Part by Wt. | Flame Retardant | Amine Catalyst | Density | Air Flow | Flammability* |
|---|---|---|---|---|---|
| 12 | Invention Mixture | 0.22 | 1.44 lb/ft$^3$ | 7.2 | Pass |
| 13 | Compound I | 0.21 | 1.43 lb/ft$^3$ | 7.4 | Fail |
| 15 | Mixture of Pentabromo-Diphenyl Ether/ Aromatic Phosphate Blend | 0.22 | 1.45 lb/ft$^3$ | 6.1 | Pass |

*Flammability of foams tested per Bulletin 117, California Department of Consumer Affairs, Bureau of Home Furnishings.

As these data demonstrate, the mixture of this invention was found to be more effective than Compound I and another commercially used flame retardant when tested under similar conditions.

EXAMPLE 7

Reaction Injection Molded Polyurethane

Flame retardant was added to the B Component of Mobay Baydur 730 reaction injection molding polyurethane resin. A half-inch thick plaque of this material having an overall density of 37 lb./ft$^3$ was prepared. Half-inch by half-inch specimens met the UL-94 flammability test V-O requirement with a flame retardant content of 15% as shown by the data in Table IV.

TABLE IV

| Flame Retardant | Average Burn Time-UL-94 Flammability Test | Heat Distortion Temperature* |
|---|---|---|
| 15% Invention Mixture (Example 1) | 0 sec. | 58° C. @ 66 psi |
| 15% Antiblaze 19** | 0.4 | 50° C. @ 66 psi |

*½ × ½" specimens
**An alicyclic phosphorous flame retardant available from Mobil Chemical which is described in U.S. Pat. Nos. 3,789,091 and 3,849,368.

EXAMPLE 8

Use as a Secondary Plasticizer

Polyvinyl chloride was compounded with a series of primary and secondary plasticizers, including the Invention Mixture of Example 1, on a two-roll mill to an even thickness sheet from which a series test specimens were cut or stamped. The basic formulation is given in Table V.

TABLE V

| Component | Parts by Weight |
|---|---|
| PVC resin | 100 |
| Primary Plasticizer | 60 |
| Secondary Plasticizer | |
| Epoxidized Soya Oil | 5 |
| Stabilizer | 3 |
| Antimony Oxide | 4 |
| Stearic Acid | 0.5 |

A total plasticizer level of 60 parts was maintained. Composition, tensile data, and oxygen indices (a measure of flame retardancy) are given in Table VI.

TABLE VI

| | | | | | |
|---|---|---|---|---|---|
| DOP %[1,2] | 100 | 50 | — | 50 | — |
| Kronitex 100%[2] (FMC Corp.) | — | 50 | 100 | — | — |
| Invention Mixture[2] % | — | — | — | 50 | 100 |
| Sb$_2$O$_3$[3] % | 2.3 | 2.3 | 2.3 | 2.3 | 2.3 |
| Tensile | | | | | |
| Stress at yield, psi | 2300 | 2650 | 2870 | 2460 | 2750 |
| Stress at 100% strain, psi | 1160 | 1350 | 1720 | 1330 | 1870 |
| Strain at break, % | 327 | 327 | 315 | 324 | 306 |
| Oxygen Index | 28 | 30 | 33 | 33 | 40 |

[1]Primary Plasticizer.
[2]% of total plasticizer
[3]% of total formulation

As these data demonstrate, the mixture of this invention performs adequately as a secondary plasticizer while greatly enhancing flammability test performance.

EXAMPLE 9

Use As a Flame Retardant for Textile Fibers

A woven 100% polyester fabric weighing approximately 5 oz./yd$^2$ was backcoated with the composition given in Table VII.

TABLE VII

| | |
|---|---|
| Water | 30 parts by weight |
| Surfactant | 0.1 |
| Invention Mixture | 16.6 |
| Acrylic Latex Emulsion | 43.0 |
| Defoamer | 0.1 |
| Acrylic Thickener | 2.5 |
| NH$_4$OH (28%) | 0.5 |

A knife blade was used to achieve a uniform coating thickness. Upon drying, the flame retardant comprised 10% of the total weight (fabric and backcoating). The backcoated fabric met the flammability criteria of Motor Vehicle Safety Standard 302.

EXAMPLE 10

Use as a Flame Retardant for Poly(Methyl)(Methacrylate)

Forty grams Rohm and Haas Plexiglas V-920 poly(methylmethacrylate) was processed at 200° C. and 75 rpm for 10 minutes in a Brabender Plasticorder. A total of 7.2 grams Invention Mixture (Example 1) and tris(dibrommopropyl) phosphate were respectively added slowly to separate samples during the first five minutes. The compounded plastics were pressed to ⅛" thickness for five minutes at 350° F. Upon cooling the plaques were cut into specimens for flammability testing. PMMA containing Invention Mixture and tris-(dibromopropyl)phosphate each met UL-94 V-2 requirements.

What is claimed is:

1. A flame retardant non-mutagenic halogenated alkyl phosphate ester mixture consisting essentially of compounds of the formula:

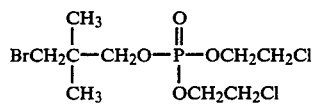 (I)

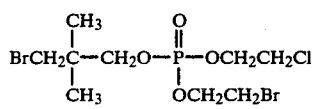 (II)

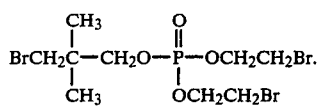 (III)

2. A mixture, as claimed in claim 1, wherein the ratio of compounds (I):(II):(III), as determined by vapor phase chromatographic area analysis, is about 1.0:1.5:1.0.

3. A mixture, as claimed in claim 1, and further comprising an effective amount of an acid stabilizer.

4. Polymer compositions having incorporated therein an effective amount of a flame-retardant nonmutagenic halogenated alkyl phosphate ester mixture consisting essentially of compounds of the formula:

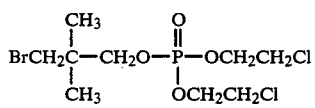 (I)

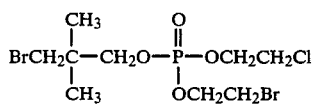 (II)

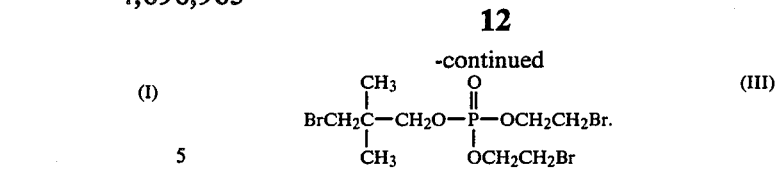 (III)

5. Polyurethane polymer compositions having incorporated therein an effective amount of a flame-retardant non-mutagenic halogenated alkyl phosphate ester mixture consisting essentially of compounds of the formula:

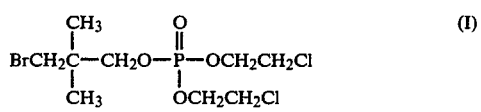 (I)

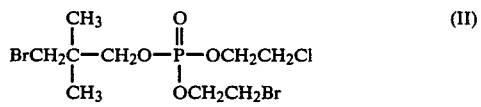 (II)

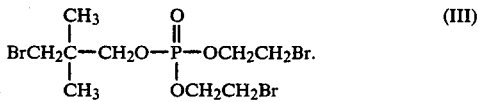 (III)

6. Polyurethane polymer compositions, as claimed in claim 5, wherein the ratio of compounds (I):(II):(III), as determined by vapor phase chromatographic area analysis, is about 1.0:1.5:1.0.

7. Polymer compositions, as claimed in claim 4, wherein the polymer is a member selected from the group consisting of polyurethane foams, reaction injection molded polyurethanes, polyvinyl chloride, polyesters, and poly-(methylmethacrylates).

8. Polyurethane polymer compositions, as claimed in claim 5, and further comprising an effective amount of an acid stabilizer.

* * * * *